(12) United States Patent
Gillessen et al.

(10) Patent No.: US 8,883,233 B2
(45) Date of Patent: Nov. 11, 2014

(54) ANIMAL FEED COMPOSITION

(75) Inventors: Hurbert Jean Marie Francois Gillessen, Lanaken (BE); Christian Rebiere, L'Herrn (FR)

(73) Assignee: Veijlen N.V., Curacao (AN)

(*) Notice: Subject to any disclaimer, the term of this patent is extended or adjusted under 35 U.S.C. 154(b) by 322 days.

(21) Appl. No.: 13/549,119

(22) Filed: Jul. 13, 2012

(65) Prior Publication Data

US 2012/0283308 A1    Nov. 8, 2012

Related U.S. Application Data

(62) Division of application No. 13/064,818, filed on Apr. 19, 2011, now abandoned, which is a division of application No. 10/574,271, filed as application No. PCT/EP2004/010983 on Sep. 28, 2004, now abandoned.

(30) Foreign Application Priority Data

Oct. 3, 2003    (WO) ................. PCT/EP03/11171

(51) Int. Cl.

| | |
|---|---|
| *A23K 1/18* | (2006.01) |
| *A23B 4/00* | (2006.01) |
| *A23L 1/31* | (2006.01) |
| *A01N 43/38* | (2006.01) |
| *A61K 31/40* | (2006.01) |
| *A01N 37/10* | (2006.01) |
| *A61K 31/19* | (2006.01) |
| *A61K 31/405* | (2006.01) |
| *A61K 31/404* | (2006.01) |
| *A23K 1/16* | (2006.01) |
| *C07D 209/18* | (2006.01) |
| *A61K 31/7056* | (2006.01) |
| *A61K 31/4045* | (2006.01) |
| *A23K 1/165* | (2006.01) |

(52) U.S. Cl.
CPC ............ *A23K 1/1625* (2013.01); *A61K 31/405* (2013.01); *A23K 1/188* (2013.01); *A61K 31/404* (2013.01); *C07D 209/18* (2013.01); *A61K 31/7056* (2013.01); *A61K 31/4045* (2013.01); *A23K 1/184* (2013.01); *A23K 1/165* (2013.01); *A23K 1/1826* (2013.01); *A23K 1/1893* (2013.01); *Y10S 426/805* (2013.01); *Y10S 426/807* (2013.01)
USPC .............. 426/2; 426/641; 426/805; 426/807; 514/419; 514/569; 514/571

(58) Field of Classification Search
USPC .......................................................... 426/2
See application file for complete search history.

(56) References Cited

U.S. PATENT DOCUMENTS

| | | | |
|---|---|---|---|
| 2,925,341 A * | 2/1960 | Kaemmerer .................. 514/419 |
| 4,025,650 A | 5/1977 | Gans et al. | |
| 4,650,789 A | 3/1987 | Pollack et al. | |
| 4,687,763 A | 8/1987 | Wurtman et al. | |
| 5,210,215 A | 5/1993 | Politi et al. | |
| 5,958,964 A | 9/1999 | Pappolla | |
| 6,017,946 A | 1/2000 | Posner et al. | |
| 2002/0016354 A1 | 2/2002 | Jensen et al. | |
| 2002/0155163 A1 | 10/2002 | Benjamin et al. | |
| 2003/0195244 A1 | 10/2003 | Hsieh et al. | |

FOREIGN PATENT DOCUMENTS

| | | | |
|---|---|---|---|
| CN | 1255349 A | 6/2000 | |
| CN | 1408397 A | 4/2003 | |
| CN | 1440744 A | 9/2003 | |
| DE | 19739763 A1 | 9/1999 | |
| DE | 10109798 A1 | 9/2002 | |
| EP | 0514373 B1 | 2/1990 | |
| EP | 0482715 A1 | 10/1991 | |
| EP | 1064941 A1 | 1/2001 | |
| FR | 2746313 A1 | 9/1997 | |
| GB | 1475861 A | 6/1977 | |
| GB | 1535778 A | 12/1978 | |
| JP | 60-161920 | 8/1985 | |
| JP | 60161920 A | 8/1985 | |
| JP | 60-199801 | 10/1985 | |
| JP | 60199801 A | 10/1985 | |
| JP | 2001-026579 | 1/2001 | |
| JP | 2001026579 A * | 1/2001 | |
| JP | 2002-281914 | 10/2002 | |

(Continued)

OTHER PUBLICATIONS

Laron, Pathol, Oct. 2001, 54(5): p. 311-316, Insulin-like growth factor 1 (IGF-1): a growth hormone.*
JP2001026579 A Machine translation.*
Lissoni et al., Total pineal endocrine substitution therapy (TPEST) as a new neuroendocrine palliative treatment of untreatable metastatic solid tumor patients: A phase II study (11-19-20012).*
International Search Report (PCT/ISA/210).
Lissoni et al., "Total pineal endocrine substitution therapy (TPEST) as a new neuro endocrine palliative treatment of untreatable metastatic solid tumor patients: A phase II study", Neuroendocrinology Letters Nos. 3/4, Jun.-Aug., vol. 24, 2003.

(Continued)

*Primary Examiner* — Rena L Dye
*Assistant Examiner* — Assaf Zilbering
(74) *Attorney, Agent, or Firm* — TraskBritt, P.C.

(57) ABSTRACT

Disclosed is an animal feed composition that comprises free indole acetic acid (free IAA) or a derivative thereof. Also disclosed is a method for enhancing animal growth by feeding the animal with a composition according to the invention. Further disclosed is the use of free IAA or a derivative thereof in a method of therapy of animals in need of a growth-promoting treatment, such as immunocompromised animals, animals with a growth deficit or slow-growing animals. Disclosed is the use of free IAA or a derivative thereof for the preparation of a therapeutical composition for increasing the growth rate and/or the feed conversion rate and/or the immunity of animals in need of such a treatment, in particular, immunocompromised or slow-growing animals. A composition may be in the form of a food or feed supplement.

21 Claims, No Drawings

(56) References Cited

FOREIGN PATENT DOCUMENTS

| JP | 2002281914 A | 10/2002 |
|----|--------------|---------|
| SE | 8200724 A | 9/1983 |
| SE | 8200724-6 A | 5/1987 |
| WO | 8904659 A1 | 6/1989 |
| WO | 9307870 A1 | 4/1993 |
| WO | 9401121 A1 | 1/1994 |
| WO | 0164205 A2 | 9/2001 |
| WO | 0164205 A3 | 9/2001 |
| WO | 02080906 A1 | 10/2002 |
| WO | 03080068 A1 | 10/2003 |
| WO | 2005039546 A3 | 5/2005 |

OTHER PUBLICATIONS

Huang, Xiaoming, Foreign Medical Sciences (section of pediatrics), Mar. 2000, pp. 57-58, vol. 27, No. 2.

Zang, Wundi et al., Cereal & Feed Industry, 1997, pp. 23-24, No. 2.

Nachshon-Kedmi et al, Indole-3-carbinol and 3,3'-diindolylmethane induce apoptosis in human prostate cancer cells, Food and Chemical Toxicology, Jun. 2003, pp. 745-752, vol. 41, No. 6.

Rossiter et al., Halogenated indole-3-acetic acids as oxidatively activated prodrugs with potential for targeted cancer therapy, Bioorganic & Medicinal Chemistry Letters, 2002, pp. 2523-2526, vol. 12, No. 18.

Folkes et al., 5-Fluoroindole-3-acetic acid: a prodrug activated by a peroxidase with potential for use in targeted cancer therapy, Biochemical Pharmacology, 2002, pp. 265-272, vol. 63, No. 2.

Fahey et al., The chemical diversity and distribution of glucosinolates and isothiocyanates among plants, Phytochemistry, 2001, pp. 5-51, vol. 56.

* cited by examiner

ANIMAL FEED COMPOSITION

CROSS-REFERENCE TO RELATED APPLICATIONS

This application is a divisional application of U.S. patent application Ser. No. 13/064,818, filed Apr. 19, 2011, pending, which application is a divisional application of U.S. patent application Ser. No. 10/574,271, filed on Mar. 14, 2007, which is a national phase application of PCT/EP2004/010983 filed on Sep. 28, 2004, which claims priority to PCT/EP03/11171 filed on Oct. 3, 2003, the entire contents of each of which are hereby incorporated herein by reference.

TECHNICAL FIELD

The invention relates to an animal feed composition that comprises free indole acetic acid (free IAA) or a derivative thereof. The invention also relates to a method for enhancing animal growth by feeding the animal with a composition according to the invention. The invention also relates to the use of free IAA or a derivative thereof in a method of therapy of animals in need of a growth-promoting treatment, such as immunocompromised animals, animals with a growth deficit or slow-growing animals. The invention also relates to the use of free IAA or a derivative thereof for the preparation of a therapeutical composition for increasing the growth rate and/or the feed conversion rate and/or the immunity of animals in need of such a treatment, in particular, immunocompromised or slow-growing animals. A composition according to the invention may preferably be in the form of a food or feed supplement.

BACKGROUND

Limited supply of conventional food protein is a major problem facing a rapid increase in world population. Of particular importance is the production of animals that contain proteins having essential amino acids required by humans. Due to limited production facilities and lack of improvement in production technology, increase in animal protein production does not seem to be proportionate the increase in world population.

Therefore, it appears highly desirable to improve the productivity of animal protein production. One of the means to improve the productivity is to develop feed compositions that enhance animal growth.

It is known that the growth rate of animals can be accelerated by administration of certain classes of substances such as antibiotics, surfactants, and estrogens. The administration of each of these classes of substances had disadvantages, however, which have prevented their universal acceptance. Thus, it is believed that antibiotics and surfactants, while effective under certain conditions, principally act to suppress diseases and do not elicit a true growth response. It is for that reason that such use of antibiotics will be limited in Europe, whereas it is under debate in the USA and Asia.

Also, the use of estrogens as growth-promoting agents presents certain inherent difficulties and hazards. Thus, estrogens frequently downgrade the animal to which they are administered. Another disadvantage is that some of the estrogenic material may remain in the edible portions of the animal and could presumably produce an adverse effect on an individual when consumed. Further, the known substances have principally been administered by injection or implantation procedures, which are both costly and time-consuming and are often disliked by consumers.

DISCLOSURE

Provided is an animal feed composition. Also provided is a feed composition that would enhance animal growth. Further provided is a method for enhancing animal growth by feeding the animal with the feed composition. Provided is a method for the preparation of an animal feed composition.

It has now been found that the disadvantages of the prior art substances and methods can be overcome, and that the growth of non-human animals can be enhanced by orally administering free indole acetic acid (free IAA) or a derivative thereof to animals in conjunction with their normal feed or drinking water.

DETAILED DESCRIPTION

Free IAA and its derivatives are known compounds. Free IAA is a naturally occurring plant growth phytohormone, which has been extensively studied. In plants, most of the IAA occurs in a conjugated form (Slovin et al. 1999, *Biochemistry and Molecular Biology of Plant Hormones*, Elsevier, Amsterdam, pp. 115-140), either conjugated to sugars via ester linkages or to amino acids and peptides via amide linkages.

The term "free IAA" is used herein to indicate that the free IAA is in the free or acid form, whereas the term "conjugated IAA" refers to IAA that is conjugated via ester linkages or via amide linkages.

As long ago as 1956, the effects of free IAA on humans were studied, and it was shown that single doses of 0.1 g/kg were non-toxic (A. Mirsky and D. Diengott, Hypoglycemic action of indole-3-acetic acid by mouth in patients with diabetes mellitus, *Proc. Soc. Exp. Biol. Med.* 93:109-110, 1956). In 1964, it was found that photo-oxidation products of free IAA acted as growth inhibitors of micro-organisms (C. Still, T. Fukuyama and H. Moyed, Inhibitory Oxidation Products of Indole-3-acetic acid, *J. Biological Chemistry* 240 6:2612-2618, 1964).

Also, the medical use of free IAA and some of its derivatives has previously been described. EP 1.296.676 describes the use of free IAA as a pharmaceutical, in particular, for treating neoplastic disease in humans. WO 02/080906 describes the use of free IAA for treating endometriosis in women. Nachson et al. (*Food and Chemical Toxocology* 41:745-752) reported the effect of some free IAA derivates (indole-3-carbinol and 3,3'-diindolylmethane) on the proliferation and induction of apoptosis in human prostate cancer cell lines whereas Rossiter et al. (*Bioorganic & Medicinal Chemistry Letters* 12:2523-2526) as well as Folkes et al. (*Biochemical Pharmacology* 63:265-272) described the use of free IAA and some derivatives in enzyme-prodrug directed cancer therapies.

It has now been unexpectedly found that free IAA or a derivative thereof effects a remarkable growth-promoting response in non-human animals, particularly farm animals such as fish, poultry, cattle and swine or pet animals such as horses, cats, dogs, rabbits and fish. Provided is a method of raising non-human animals by administering free IAA to the animal, preferably via a feed.

The free IAA or a derivative thereof may be fed to the animal and is most effective when administered within clearly defined concentrations in the animal feed and/or water. Injection and/or implantation is unnecessary and the animals orally ingest the free IAA or a derivative thereof of their own free choice with their feed.

According to one embodiment, an animal feed composition that enhances animal growth is provided that comprises free IAA or a derivative thereof. Such an animal feed composition can be a conventional feed composition supplemented with free IAA or a derivative thereof in a concentration sufficient to allow a daily intake of between 25 and 1000 micrograms per kg life weight per day (ug/kg LW/day). Such a feed composition may then contain between 0.2 mg and 10 g free IAA or a derivative thereof per kg feed.

Particularly good results were obtained when directly feeding to an animal a feed composition containing more than 0.24 mg free IAA or a derivative thereof per kg feed, such as a feed composition containing more than 0.30 mg free IAA or a derivative thereof per kg feed, or a feed composition containing more than 0.40 mg free IAA or a derivative thereof per kg feed, such as more than 0.6, 0.8, 1, 5, 10, 20, 30, 50, 100, 200 or 500 mg free IAA or a derivative thereof per kg feed.

The disclosure, therefore, relates to an animal feed composition comprising more than 240 micrograms of free IAA or a derivative thereof per kilogram.

The upper limit of the concentration of free IAA or a derivative thereof is, for a large part, determined by the intended use. The feed composition may be in the form of a feed or food additive that has to mixed into the animal feed at a convenient rate. In this case, the concentration of free IAA or a derivative thereof may be as high as 10%, i.e., 100 g/kg. The feed composition may also be in the form of a ready-to-use mixture. In that case, the upper limit is determined by the desired dose for the animal, once the daily intake of feed of the animal is known. In daily practice, feed compositions containing 1, 2, or 4% (10 to 40 g/kg) free IAA or a derivative thereof proved to be most practical for storage in the form of a stock feed additive. A preferred storage form of a feed composition to be mixed into a ready-to-use feed or into a feed additive is, therefore, a mixture of about 1-4% free IAA or a derivative thereof with other dry material suitable for ingestion.

The invention, therefore, relates to a feed composition comprising up to 40 g of free IAA or a derivative thereof per kilogram.

Preparations containing between 100 mg and 1000 mg, such as 500 mg free IAA or a derivative thereof/kg feed additive were most practical when used to correctly dose the free IAA or a derivative thereof into the ready-to-use feed composition.

The invention, therefore, also relates to a feed composition comprising between 100 and 1000 mg of free IAA or a derivative thereof per kilogram.

A skilled person will appreciate that the amount of free IAA in the ready-to-use feed has to be adjusted in order to supply the animal with an effective amount of free IAA. In order to adjust the free IAA concentration in the feed so that a certain daily intake of free IAA is achieved, an estimate has to be made of the feed intake of an animal or animal group. A skilled person is aware of the feed intake of a particular kind or group of animal(s), usually the feed intake per day is between 0.5 and 10% of the body weight of the animal, with occasional exceptions as high as 20%, such as, for instance, in young chickens. An animal will normally ingest twice the unit volume of water as it will ingest feed. Accordingly, an animal will ingest the same amount of free IAA when fed with a feed composition containing 10 milligrams free IAA/kg as it will by drinking water with a concentration of 5 mg/l or a combined concentration of 2.5 mg/l in water plus 5 mg/kg in feed.

An animal feed composition as used herein comprises a composition for animal nutrition, in solid or in liquid form. Feed is the main source of energy and of nutrition for animals and is usually of animal or plant origin. Thus, feed may be defined as a substance with sufficient nutritional value to allow for growth and maintenance of adequate body conditions of an animal. In a typical embodiment, an animal feed composition consists of pellets, meal, grains, extruded or expanded grains, tablets, powder or bolus forms. A particularly advantageous feed composition comprises a foodstuff selected from the group consisting of dry forages and roughages, energy feeds, protein feeds, mineral feeds, vitamin feeds, yeast products, normal premix, cornmeal, cotton seed, wheat gluten, maize silage, rutabaga, sugar beet pulp, apple pulp, ryegrass, fescue grass, alfalfa feed concentrate and feed supplement. The free IAA or a derivative thereof may be mixed with any suitable base feed material, such as rape seed, cotton seed, soybean, fish meal, wheat bran, wheat feed meal, minerals, vitamins and binders or prepared as a premix with, for example, amino acids, salts, phosphorous or cornmeal. In one particularly advantageous embodiment, the feed or feed additive is in a form and/or composition approved by a governmental institution such as the FDA, the U.S. Department of Agriculture, or the Canadian Food Inspection Agency. In Europe, the Task Force on animal feeding of the Codex Alimentarius Commission (CAC), as well as the Animal Welfare Act (AWA), provide definitions of animal feed. In one advantageous embodiment, the invention concerns an animal feed within the definition of "animal feed" in section 201(x) of the FFDCA, supplemented with free IAA.

Free IAA or a derivative thereof is conveniently incorporated directly in the animal feed and/or water. Any suitable method for dispersing the material in the feed can be used. The amount of free IAA or a derivative thereof added to the animal feed and/or water may be varied within the limits stated in order to obtain the maximum benefits.

The invention, therefore, comprises a method for the preparation of animal feed comprising the steps of providing an animal feedstuff and mixing the feedstuff with an effective dose of free IAA.

The composition may be in the form of a capsule, but other dosage forms, preferably oral dosage forms, such as tablets, suspensions, emulsions, fluids, powders, lozenges, pastilles, pills, etc., are also possible. The composition may, for example, take the form of a feed supplement, a feed additive or a pharmaceutical composition.

There is also provided a method for promoting the growth of non-human animals and/or improving the feed efficiency and/or the feed conversion rate and/or the immunity of a non-human animal that comprises administering to the animals an animal feed composition according to the invention. Comprised herein is a method wherein a liquid such as water containing more than 120 ug free IAA or a derivative thereof per liter fluid is administered to the animals, such as 240, 500, or more than 1000 ug/l.

Feedstuffs and/or water supplemented with free IAA or a derivative thereof according to the invention are particularly suitable for the commercial rearing of farm animals such as fish, cattle, poultry and swine. They may also be used for pet animals such as rabbits, horses, birds such as pigeons, fish such as koi fish, cats and dogs. By utilizing such supplemental diets, it is not only possible to greatly accelerate the growth of non-human animals but also the efficiency of feed conversion (i.e., the number of kg of feed needed to produce one kg gain in animal weight) is greatly increased, resulting in greater economic benefits.

The animal feed composition and methods herein may also be applied to animals that have a growth deficit. In animal experiments, it was shown that the weight of poorly growing animals increased to normal levels when fed with free IAA or a derivative thereof. These experiments are illustrative of the fact that the compounds and methods of the invention lead to an increased appetite and/or improved feed conversion.

The term "growth deficit" in this respect is to be regarded as a growth that substantially lacks behind the normal growth of the species. Such animals exhibit a life weight that is more than 10%, such as more than 25%, 40%, 60% or 80% below the median of the normal weight distribution of animals with the same age within the species.

The animal feed composition and methods according to the invention may also be applied to immunocompromised animals. Immunocompromised animals are herein defined as non-human animals with an impaired or weakened immune system. Such animals are usually characterized by a lowered level of IGF-1 in their serum. Lowered IGF-1 serum levels are herein defined as levels of IGF-1 that are more than 10% below the normal median of the healthy subjects in the species, such as more than 25%, 40%, 60% or more than 80%. A weakened immune system is often the cause of an elevated death rate caused by disease or adverse living conditions.

The invention is also useful for the treatment of animals showing various other indications that are associated with a lowered serum level of IGF-1 Provided is a means for increasing the IGF-1 serum level in a non-human animal suffering from a condition associated with a lowered IGF-1 serum level.

This is achieved by administering free IAA or a derivative thereof to a non-animal in need of such a treatment. Accordingly, the invention thus relates to the use of free IAA and a derivative thereof for the preparation of a therapeutical composition for increasing the growth rate and/or immunity in immunocompromised animals and/or animals with a growth deficit. This may lead to an increased body weight of the animal and/or a reduced death rate caused by diseases or adverse living conditions.

It was found that for the various indications as exemplified herein, there are optimal amounts of free IAA or a derivative thereof to be administered. In general, in order to further increase the growth rate of healthy and normal growing animals, a daily intake of free IAA of between 25 and 1000, more in particular between 50 and 500, ug/kg LW/day is sufficient. Particularly good results may be obtained when administering 150 to 500 ug free IAA/kg LW/day. As exemplified herein after, African catfish showed a remarkably improved feed conversion rate of 7% when an average of 218 ug free IAA/kg LW/day was administered. Healthy poultry gained 18% more weight in 5 weeks when fed with a dose of 400 ug free IAA/kg LW/day. Comparable results were obtained in cattle and swine farms.

In order to increase the growth rate of animals that exhibit a growth deficit (in particular, farm or pet animals), a slightly higher dose is often required. Particularly good results were obtained with a dose of 50 to 1000 ug free IAA/kg LW/day, in particular, 250 to 1000 ug free IAA/ LW/day, more in particular, 400 to 1000 ug free IAA/kg LW/day such as 500 or 750 to 1000 ug free IAA/kg LW/day during a short period of time such as less than 6 weeks or 4 weeks but, more in particular, less than 3 weeks, such as 2 weeks.

Optimal dosage of free IAA or a derivative thereof may be determined empirically, and may, within the limits defined herein, depend to some extent on the particular type of feed, species and farming conditions. A person skilled in the art knows how to set up a schedule for such dosing experiments, the experimental design of Example 7 may be helpful therein.

The key compound is thus free indole acetic acid. However, equivalent results may be achieved by using derivatives of free IAA. "Derivatives of free IAA" are herein defined as compounds that lead to an increased level of free IAA in the body of the non-human animal in comparison to the level of free IAA in the same animal body prior to administration of the compound. These derivatives can be divided into various categories.

One category of derivatives of free IAA is conjugated IAA. Conjugated IAA may appear in the form of IAA conjugated via ester linkages, for example, to sugars such as, for example, IAA-glucose, IAA-alfa-aspartic acid 1N-glucoside, IAA-inositol, IAA-myoinositols or IAA linked to various other carbohydrates. IAA may also be conjugated via amide linkages, for instance, to amino acids and peptides. Examples thereof are acetamide, alfa-leucine, alfa-alanine, alfa-aspartate (most important conjugate of IAA in plants), alfa-glutamate, alfa-lysine, alfa-glycine, alfa-valine, alfa-phenylalanine or slow-release amide conjugates with lysine or tryptophan. Conjugation with peptides is common, whereas, conjugates with other amino acids also occur in different plants. In addition, this group comprises 3-acetonitrile derivatives, which easily are converted into the corresponding acid, like indole-3-acetonitrile that decomposes in free IAA, both chemically (under basic conditions) and enzymatically (by nitrilase activity).

In order to be useful in the invention, this conjugated IAA must be converted to free IAA. This may be achieved by simultaneous admission of enzymes, such as esterases, amidases or nitrilases, to the animal. This may, for instance, be achieved by admixing enzymes together with the conjugated IAA into the animal feed composition.

The invention thus relates to an animal feed composition as described above, additionally comprising an enzyme capable of converting a derivative of free IAA into free IAA.

However, the conjugated IAA may also be added to the feed and/or administered to the animal as such, thereby relying on the enzyme activities naturally present in the circulation or gastro-intestinal tract of the animal for the conversion of conjugated IAA into free IAA.

Free IAA is liberated from the amides by amidases (amidohydrolysases). Free IAA may be released from the glucosides by glucosidases. In plants, considerable amounts of conjugated IAA can be present, which can be liberated either by enzymatic hydrolysis (such as glucosidases or amidases) or chemical hydrolysis. Of the total IAA pool in plants, amide-linked IAA in general constitutes 90%, whereas approximately 10% is ester linked and less than 1% is free IAA. In plants, levels of free+bound free IAA as high as about 1.2 ug/g Dry Weight may be found such as in nine-day-old Arabidopsis. Later in the life cycle of the plant, these levels drop. A maximum of about 1% of this is free IAA.

A variety of hydroxylated, phosphorylated, methoxylated, N-oxides and N-methylated indole derivatives can also be found in plants. These compounds can also be converted into free IAA, either in the stomach, gut, liver or elsewhere in the body. This conversion can be enzymatic or chemical. Thus, the invention also relates to these compounds that can be converted to free IAA, either directly or indirectly, through metabolic conversion. These so-called precursors are, for example, 4-hydroxy-IAA, 4-methoxy-IAA, 5-hydroxy-IAA, 5-methoxy-IAA, 6-hydroxy-IAA, 6-methoxy-IAA, 7-hydroxy-IAA, and 7-methoxy-IAA.

Furthermore, the term "derivative" may also comprise IAA with other substituents, compounds that may be either naturally occurring or synthetic. The term "naturally occurring" also encompasses the result of metabolism by living cells such as plants, micro-organisms, mammalian cells and the human or animal body. In nature, halogenated indole alkaloids can be found, particularly in marine organisms (i.e., 6-bromoindigotin). All types of substituents can synthetically be introduced on the aromatic ring, e.g., methyl, amino, nitro, fluoride, chloride, bromide, and iodide on the positions 4, 5, 6 and 7. These compounds may all be used to increase the level of free IAA in an animal.

The term "derivatives" may also encompass precursors from which free IAA and analogues as listed above could be formed, such as tryptophan, 4-hydroxytryptophan, 4-methoxytryptophan, 5-hydroxytryptophan, 5-methoxytryptophan, 6-hydroxytryptophan, 6-methoxytryptophan, 7-hydroxytryptophan, 7-methoxytryptophan, hypaphorine, tryptamine, 4-hydroxytryptamine, 4-methoxytryptamine, psilocin(4-hydroxy, dimethyl tryptamine), psilocybin(4-phosphate, dimethyl tryptamine), baeocystin, serotonin(5-hydroxytryptamine), 5-methoxytryptamine, bufotenine(dimethylserotonine), O-methylbufotenine, melatonin(5-methoxy, acetamide function on tryptamine $NH_2$), 6-hydroxytryptamine, 6-methoxytryptamine, 7-hydroxytryptamine, 7-methoxytryptamine. Other naturally occurring precursors for free IAA formation are indole butyric acid and indole-3-pyruvate.

The term "derivatives" may also encompass compounds that are analogues or metabolites of free IAA that may be converted back into free IAA. These compounds also encompass the above mentioned 4-, 5-, 6- and 7-hydroxy- and methoxy-derivatives. These compounds are, for example, indole, indole-3-acetaldehyde, indole-3-ethanol, indole-3-aldehyde, indole-3-methanol, indole-3-carboxylic acid, 3-methylindole (skatole), indole-3-acetaldoxime, 3-aminomethylindole, N-methylaminomethylindole, Gramine (N-dimethylaminomethylindole).

The term "derivatives" may also encompass compounds with changed indole chromophore, such as indoxyls (indicans), indoleninones, 3-methylene-2-oxindole, abrine, isotan B, isatin, indican, indigo, indurubin, indigotins, 3-indolylmethyl(skatolyl), niacin and 2-oxindole-3-acetic acid.

The term "derivatives" may also encompass compounds that are commonly found in plants or vegetable tissue, such as 3-methylene-2-oxindole, oxindole-3-methanol, oxindole-3-aldehyde, oxindole-3-carboxylic acid and 3-methyloxindole.

Furthermore, the invention also relates to the use of conjugates (esters and amides) of other natural IAA derivatives such as 2-oxindole derivatives and 4-, 5-, 6- or 7-hydroxy-derivatives: dioxindole-3-acetic acid, 3-O-beta-glucosyl-dioxindole-3-acetic acid 7-hydroxy-2-oxindole-3-acetic acid-7'-O-beta-d-glucopyranoside, gleopyrasonyl-beta-1,4-glucopyranosyl-beta-1-N-oxindole-3-acetyl-N-aspartic acid, glucopyranosyl-beta-1-N-oxindole-3-acetyl-N-aspartic acid, 2-indolone-3-acetyl aspartic acid, 3-(O-beta-glucosyl)-2-indolone-3-acetyl aspartic acid, 3-hydroxy-2-indolone-3-acetyl aspartic acid, indole-3-glycerophosphate (decomposes in free IAA under basic conditions), indole-3-glycerol (decomposes into free IAA under basic conditions), glucosinolates, such as indole-3-ylmethyl glucosinolate(glucobrassicin), 4-hydroxyindol-3-ylmethyl glucosinolate(4-hydroxyglucobrassicin), 1-acetyl-indol-3-ylmethyl glucosinolate(1-acetyl-glucobrassicin), 1-methoxyindol-3-ylmethyl glucosinolate(neoglucobrassicin), 4-methoxyindol-3-ylmethyl glucosinolate, (4-methoxyglucobrassicin), 1-sulfo-indol-3-ylmethyl(glucobrassicin-1-sulfate), which are converted into indole derivatives by myrosinases(thioglucosidases).

In general, derivatives of free IAA are preferably molecules that can be synthesized into free IAA in one step, either by chemical synthesis or by enzymatic conversion. Examples of such derivatives are indole-3-acetaldehyde (IAAld) that can be converted into free IAA by action of IAAld oxidase (AAO1) or indole-3-acetonitrile (IAN) that can be converted into free IAA by nitrilases NIT1, NIT2, or NIT3 (Bartel et al., *J. Plant Growth Regul.* (2001) 20:198-216). Alternatively, derivatives of free IAA may be molecules that can be synthesized into free IAA in two steps. Examples of such molecules are indole glucosinolate that involves the action of an enzyme known as myrosidase, indole-3-acetaldoxime (IAOx) and many other precursors that are now apparent for a person skilled in the art. Alternatively, derivatives of free IAA may be molecules that can be synthesized into free IAA in three or more steps.

The invention, therefore, relates to an animal feed composition comprising a derivative of free IAA wherein the derivative can be converted into free IAA in more than three steps, preferably in three, more preferably in two and most preferably in one step.

It may be apparent now for the skilled person that the dose of a derivative of free IAA in the animal feed is to be adjusted in order to yield free IAA concentrations in the animal body that correspond to the ranges given herein for free IAA. This has to account for conversions that are mostly not entirely complete and losses during production when prepared chemically. Concentrations of derivatives may, therefore, best be established empirically, the experimental set-up as outlined in Example 7 may be helpful in this respect. Consequently, when it is referred herein to a certain concentration of free IAA or a derivative thereof, it is meant that this is the concentration of free IAA or the concentration of the derivative that yields this particular concentration of free IAA in the animal. The skilled person will be aware of this and knows how to determine the proper concentrations of derivatives with the help of the teachings as provided herein.

Free IAA is readily available as a commercial product. It may be synthesized chemically or prepared in a biological way. IAA-producing micro-organisms are widespread in nature. Yeast, fungi and many bacteria, as well as plants, are known to convert precursors of IAA into free IAA. In addition to the L-tryptophan conversion by bacteria, L-tryptophan independent biochemical routes toward free IAA are also described extensively (*J. Plant Growth Regul.* (2001) 20:198-216).

A well-known bacterium capable of producing free IAA is *Azospirillum Brasilense* (AB). At the end of the growth phase in a regular fermentation process, AB is able to convert L-tryptophan into free IAA. To increase the efficiency of this conversion, a small amount of synthetic free IAA may be added to the media. Via a feedback mechanism, AB increases the conversion of L-tryptophan into free IAA.

Final concentrations of 1 gram free IAA/liter culture broth are easy to make, but even much higher concentrations are possible, depending on the micro-organism used.

After ending the fermentation, the micro-organism may be lysed and a powder enriched in free IAA may be obtained by spray drying or any other convenient way of drying the culture broth. Other techniques may be used to remove liquids partly or completely.

EXAMPLES

Example 1

Source of Free IAA

Free IAA or a derivative thereof may be obtained from any commercial source. Alternatively, free IAA may be produced in a microbiological way.

To this end, *Azospirillum Brasilense* Sp7 (ATCC) was obtained as an agar culture in a culture tube. LB medium was used to grow the strain overnight at 28° C. at 175 rpm. Glycerol was added to the culture up to 10%, mixed and divided over Nalgene creovials and frozen at −80° C. Stocks were stored at −80° C. in creovials.

To prepare a seed culture of *A. Brasilense*, one stock (1.2 to 1.8 ml) was thawed and added to 1 liter of LB medium and grown for about 20 hours at 28° C. and 175 rpm to an Optical Density (OD620 nm) of about 2.5.

A 10 liter fermentor was rinsed with water and the pH electrode was calibrated. Nine liters of LB medium was prepared and 1 g/l L-Tryptophan and 0.1 g/l free IAA was added. The medium was entered into the fermentor, together with 2 ml of anti foam. The fermentor was sterilized for 30 minutes at 121° C. After cooling down to 28° C., the O2 probe is calibrated with N2 and O2, 0% and 100% air saturation, respectively.

The seed culture is transferred to the fermentor via a flask and tubing, which are separately sterilized in an autoclave. When the addition is completed, the tubing and flask are removed and the fermentation is started with the following parameters:

| | |
|---|---|
| Stirrer speed | 400 rpm |
| Temperature | 28° C. |
| Aeration | 0.75 Nl/min |
| PH | 7 |

After 15 minutes, a sample is taken to measure the OD620 nm and check the pH. Samples are taken at certain intervals to quantify the growth of *A. brasilence*. When the growth rate declined, extra medium was added to ensure that enough biomass was formed for the production of free IAA. It was found that the production of free IAA started when the active growth phase ended and continued for a prolonged period. The course of the free IAA concentration was followed by LC-MS. When the concentration of free IAA was at a level of about 1 g/l, the fermentation was terminated and the cells were harvested and lysed by means of a nonojet homogenizer at about 1400 bar. The remaining supernatant and the lysed cells were sterilized and spray dried to yield the desired product formulation.

Example 2

Growth Rate of Poor-Growing Piglets Can be Improved with Free IAA

The trial was done in a well managed farm with 1000 sows of the Dutch Land race. Although the farm is well run, the technical performance was not optimal. There were latent problems with mortality and with growth rates of the piglets. There were too many poor-growing piglets, without a clear underlying technical or veterinary reason. There was no clear pathology to be seen on the farm.

Three groups of piglets were randomly selected at day 1 of the trial. The first (control) group consisted of normal well-growing piglets. The B group consisted of 78 poor growers, these were treated with free IAA. The X group consisted of 52 poor growers that were not treated.

The B group received free IAA in the feed, starting on day 5 of the trial. The feed for the B group was prepared by first mixing free IAA with dextrose, which was then mixed with the feed. For that purpose, 4 grams of pure free IAA (Aldrich) was mixed with 96 grams dextrose and the mixture was then dispersed in the feed. The pigs from the B group received a dosage of 500 ug free IAA/kg LW/DAY (LW=life weight), which corresponds to 12.5 mg/kg LW/DAY of the 4% free IAA/dextrose mixture.

The piglets were weaned for two days at the start of the trial. Blood samples for IGF-1 measuring were taken from each group at day 5 of the trial and at the end of the trial. Two pens (13 piglets) of the B and X groups were weighed at day 5 and at the end of the trial. Quantification of IGF-1 was performed using an immunoradiometric assay (IRMA) (DSL-5600 ACTIVE™, DSL, Germany GmbH, Germany). Infra- and inter-assay variance was: 4.0% and 9.2% for GH; 3.0% and 1.5% for IGF-1.

Already after one week of treatment, the farmer noticed a clear difference between group B and group X. The piglets in group B were looking better, the bellies were better filled and the general appearance of the piglets started to look better than in group X. This phenomenon became more pronounced when the treatment continued. There were less poor growers in the B group; skin and hair were looking much better.

At day 1 of the trial, there was no difference in IGF-1 levels between the three groups (Table 1). IGF-1 levels were low, between 0.8 and 13.1 with an average of 4.6. There was no observable difference between the (well-grown) control group and the (poor-grown) groups X and B, probably due to the stress of weaning.

At day 26 of the trial, IGF-1 levels were measured again. The B group was on the level of the healthy control group (25.3 vs. 23.6 nmol/l), which was clearly higher than the non-treated group X (17.2 nmol/l).

TABLE 1

| | IGF-1 measurement [nmol/l] | |
|---|---|---|
| | Day 1 | Day 26 |
| Control group | | |
| 1 | 0.8 | 14 |
| 2 | 4.3 | 16.6 |
| 3 | 7.9 | 25.4 |
| 4 | 6.1 | 30.3 |
| 5 | 3.9 | 31.7 |
| total | 23 | 118 |
| average | 4.6 | 23.6 |
| Treated group B | | |
| 1 | 3 | 25.2 |
| 2 | 2.7 | 28.9 |
| 3 | 6.1 | 25.5 |
| 4 | 5.3 | 29.9 |
| 5 | 5.7 | 16.9 |
| total | 22.8 | 126.4 |
| average | 4.56 | 25.28 |
| Non-treated group X | | |
| 1 | 2.9 | 11.3 |
| 2 | 4.3 | 21.6 |
| 3 | 1.6 | died |
| 4 | 13.1 | 20.8 |
| 5 | 1.3 | 15.1 |
| total | 23.2 | 68.8 |
| average | 4.64 | 17.2 |

Pen B 3 L(eft) grew on average 850 grams more than their neighbors from pen X 4 L(eft). Pen B 3 R(ight) gained on average as much weight as their neighbors from pen X 4 R(ight), but weighed 310 grams less at the start of the trial. On average, the treated group gained (for the pens that were weighed) almost 0.5 kg more over a period of 21 days (Table 2).

TABLE 2

| Pen nr | Weight (kg) at day 5 Total (kg) | Average | Weight (kg) at day 26 Total (kg) | Average | Weight gain (kg) Average |
|---|---|---|---|---|---|
| B 3L | 86 (n = 13) | 6.62 | 150 (n = 11) | 13.64 | 7.02 |
| B 3R | 88 (n = 13) | 6.77 | 167 (n = 13) | 12.85 | 6.08 |
| X 4L | 80 (n = 12) | 6.67 | 141 (n = 11) | 12.82 | 6.15 |
| X 4R | 92 (n = 13) | 7.08 | 171 (n = 13) | 13.15 | 6.08 |

After the treatment was stopped, the piglets from group B continued to perform better than group X. Piglets from group B started to look better than the non-treated group and grew better than the untreated group. These characteristics are clearly correlated with a higher IGF-1 level in the treated groups.

The results of this trial confirm that a single treatment for 14-21 days with 500 ug free IAA/kg LW/DAY effectively restores IGF-1 levels in poor-growing piglets and promotes growth up to a level of normal well-developed piglets. As a result of this treatment, pigs have caught up the lost growth and have done well during the fattening period, without the need of continuing the treatment.

Example 3

Growth of Healthy Laying Hens Can be Improved with Free IAA

In this example, normally growing animals were treated with free IAA. Growing laying hens of 10 weeks old were selected in the flock to create two groups of ten hens:

Group GB: 10 normally growing hens, not treated

Group GNA: 10 normally growing hens, treated with free IAA

The treated birds were force fed daily with a capsule with 400 ug free IAA/kg LW/DAY, which corresponds to 10 mg/kg LW/DAY of a 4% mixture of free IAA in dextrose. Treatment was continued until the hens started laying. The two groups were weighed every week.

From the first week on, an improved weight gain was seen in the treated group when compared with the non-treated group. The improvement in weight gain was consistent over the first four weeks of the trial. The group GNA was about 2 weeks in advance of the normal rearing schedule.

The last couple of weeks of the experiment were very stressful for the birds, since it was very hot, and the birds were vaccinated against ILT.

TABLE 3

| | Group GB | | Group GNA | |
|---|---|---|---|---|
| Week | Average weight (gr) | Average weight gain (gr) | Average weight (gr) | Average weight gain (gr) |
| 1 | 690.5 | | 740 | |
| 2 | 802 | 111.5 | 883 | 143 |
| 3 | 878 | 76 | 996 | 113 |

TABLE 3-continued

| | Group GB | | Group GNA | |
|---|---|---|---|---|
| Week | Average weight (gr) | Average weight gain (gr) | Average weight (gr) | Average weight gain (gr) |
| 4 | 995 | 117 | 1095 | 99 |
| 5 | 1098 | 103 | 1222 | 127 |
| total weight gain (gr) | | 407.5 | | 482 |

After one week, the weight gain already gave a clear indication that free IAA has a beneficial effect on the growth rate of normal hens. It can be concluded that free IAA has a beneficial effect on the growth of normal birds, and that free IAA can speed up the normal rearing process and deliver much stronger birds at the end of the rearing period. After 5 weeks of trial, the birds who received free IAA in their feed were 18% heavier on average than the control group that did not receive free IAA.

Example 4

Performance of Poor-Growing Laying Hens Can be Improved with Free IAA

Poor growth of laying hens constitutes a big problem in rearing hens. In this example, poor-growing birds were treated with free IAA. The flocks in the test farm did not grow uniformly, and about 10-15% of the birds had a too poor growing performance.

Growing laying hens of 10 weeks old were selected in the flock to create three groups of ten hens:

Group GB: 10 normally growing hens, not treated

Group SB: 10 poorly growing hens, not treated

Group SNA: 10 poorly growing hens, treated with free IAA

The treated birds were force fed daily with a capsule with 400 ug free IAA/kg LW/DAY which corresponds to 10 mg/kg LW/DAY of a 4% mixture of free IAA in dextrose. Treatment was continued until the hens started laying. The different groups were weighed every week.

From the first week on, an improved weight gain was seen in the treated SNA group when compared to the non-treated SB group. The improvement in weight gain was consistent over the first four weeks of the trial. The SNA group had caught back up to the schedule of normal growth and in some weeks outperformed the normal growing hens that were not treated in group GB.

The last couple of weeks of the experiment were very stressful for the birds, since it was very hot, and the birds were vaccinated against ILT.

TABLE 4

| | Group GB | | Group SB | | Group SNA | |
|---|---|---|---|---|---|---|
| WEEK | Average weight (gr) | Average weight gain (gr) | Average weight (gr) | Average weight gain (gr) | Average weight (gr) | Average weight gain (gr) |
| 1 | 690.5 | | 498.5 | | 489.5 | |
| 2 | 802 | 111.5 | 585 | 86.5 | 598 | 108.5 |
| 3 | 878 | 76 | 685 | 100 | 718 | 120 |

TABLE 4-continued

| | Group GB | | Group SB | | Group SNA | |
|---|---|---|---|---|---|---|
| WEEK | Average weight (gr) | Average weight gain (gr) | Average weight (gr) | Average weight gain (gr) | Average weight (gr) | Average weight gain (gr) |
| 4 | 995 | 117 | 790 | 105 | 885 | 167 |
| 5 | 1098 | 103 | 907 | 117 | 995 | 110 |
| total weight gain (gr) | | 407.5 | | 408.5 | | 505.5 |

After one week, the weight gain already gave a clear indication that free IAA has a beneficial effect on the growth rate of hens with a growth deficit. The group SNA shows the highest weight gain in this test period. It is concluded that free IAA may suitably be used in the treatment of hens that have a growth deficit in order to have them catch up their "lost" growth.

It can also be concluded that free IAA does not seem to induce a resistance in hens to its mode of action at the dosage of 400 ug free IAA/kg LW/DAY.

So the results of this example indicate that the use of free IAA can bring poor-growing hens back to the normal rearing schedule and prevent loss of animals for normal production, and that free IAA can deliver much stronger birds at the end of the rearing period.

Example 5

Survivors of Porcine Reproductive and Respiratory Syndrome Virus Fed with Free IAA This experiment was performed with Belgian Land Race piglets that had a history of PRRSV. The piglets were weaned at four weeks and relocated at twelve piglets per pen. IGF-1 levels from three different groups were tested at the age of five weeks.

Group P

These were the pigs with the big problems. They were looking poor, had a low weight, bad color, and some of them had Staphylococcus infections. It was the firm belief of the farmer and the veterinarian that these piglets would not survive until the end of the fattening cycle. Blood samples were taken at random from five of the twelve piglets.

TABLE 5

| Animal | IGF-1 [nmol/l] at day 1 |
|---|---|
| Piglet 1 | 2.3 |
| Piglet 2 | <0.5 |
| Piglet 3 | <0.5 |
| Piglet 4 | 2.0 |
| Piglet 5 | 1.8 |

The results of Table 5 indicate a severe impairment of the immune system as indicated by low IGF-1 levels. A clear correlation exists between poor growth and health and IGF-1 concentration. Each animal of approximately seven kilos was treated with 125 mg of a 4% free IAA composition comprising 5 mg free IAA and 120 mg NaCl and WPC 70 (Whey Protein Concentrate) for a period of ten days. The product was fed in a trough, mixed in liquid feed. All the piglets ate from the same trough. This dosage corresponds to a treatment with 715 ug free IAA/kg LW/day.

After ten days of treatment, all twelve pigs were still alive and their condition had dramatically improved. They all had a nice pink color, no more stiff hair, the ears were in normal position, no piglets suffered from Staphylococcus infection anymore. They had gained very much in weight and in muscle growth and had caught up very much to the average of the rest of the "normal" litter mates. All external signals for good health were now present.

After ten days, blood samples were taken from five randomly chosen piglets and their IGF-1 concentrations were determined. A code was added for the size of the animals (K=small; N=normal; Z=heavy).

TABLE 6

| Animal | IGF-1 [nmol/l] at day 10 |
|---|---|
| Piglet PN | 0.8 |
| Piglet PK | <0.5 |
| Piglet PZ | 4.2 |
| Piglet PK | <0.5 |
| Piglet PN | <0.5 |

The dramatic improvement in health, weight and condition of the piglets was not reflected in their IGF-1 levels. The average IGF-1 levels did not rise during the first 10 days of the trial. We assume that at that time, all the extra IGF-1 production is still used in the process of the extra growth. Yet, there is a clear link between individual weight and IGF-1 levels.

After 10 days, the free IAA treatment was stopped and the animals were held on a normal diet. Another three weeks later, blood samples were taken again from seven randomly chosen pigs from the group.

TABLE 7

| Animal | IGF-1 [nmol/l] at day 31 |
|---|---|
| Piglet 1 | 30.0 |
| Piglet 2 | 23.4 |
| Piglet 3 | 65.1 |
| Piglet 4 | 13.7 |
| Piglet 5 | 60.1 |
| Piglet 6 | 36.9 |
| Piglet 7 | 55.6 |

These results clearly show that the piglets' IGF-1 production was now considerably increased, even though the treatment was stopped.

It may be concluded that the treatment with free IAA dramatically improved the condition of the problem piglets. Their immune system eliminated the Staphylococcus infections. This improvement was not immediately (after 10 days) reflected in the IGF-1 serum concentration, but three weeks after the treatment was stopped, the IGF-1 level had risen to (almost) normal levels.

Group R

These piglets were looking the best. They received a special pre-starter feed before weaning. Five piglets was chosen at random and their IGF-1 levels were determined (Table 8).

TABLE 8

| Animal | IGF-1 [nmol/l] at day 1 |
|---|---|
| Piglet 1 | 4.3 |
| Piglet 2 | 1.0 |
| Piglet 3 | 7.3 |

TABLE 8-continued

| Animal | IGF-1 [nmol/l] at day 1 |
|---|---|
| Piglet 4 | 22.2 |
| Piglet 5 | 14.7 |

The special pre-starter seemed to boost the IGF-1 levels in this group. As from day 1, these piglets were fed a normal commercial piglet starter diet, supplemented with the same dosage free IAA as group P. Group R was growing normally. No particular signs were present. At day 10, blood samples were taken from six piglets selected at random.

TABLE 9

| Animal | IGF-1 [nmol/l] at day 10 |
|---|---|
| Piglet RK | 11.4 |
| Piglet RN | 11.4 |
| Piglet RN | 32.6 |
| Piglet RZ | 18.7 |
| Piglet RK | 9.8 |
| Piglet RZ | 10.4 |

The average IGF-1 concentration in group R rose in two weeks from 9.9 nmol/l to 15.72.

Group T

These were normal looking piglets. They received a regular piglet starter feed before weaning

TABLE 10

| Animal | IGF-1 [nmol/l] at day 1 |
|---|---|
| Piglet 1 | 2.7 |
| Piglet 2 | <0.5 |
| Piglet 3 | 0.8 |
| Piglet 4 | 0.5 |
| Piglet 5 | 3.5 |

These piglets have normal growth, but not as good as the R group. This is also reflected in the lower 1GF-1 levels.

These piglets were kept on their original piglet starter feed supplemented with the same dosage free IAA as groups P and R. Group T was also growing normally without any particular symptoms. Blood samples were taken from five piglets selected at random and their IGF-1 concentration was determined.

TABLE 11

| Animal | IGF-1 [nmol/l] at day 10 |
|---|---|
| Piglet TZ | 10.5 |
| Piglet TN | 6.0 |
| Piglet TN | 3.1 |
| Piglet TN | 10.9 |
| Piglet TZ | 16.3 |

The average IGF-1 concentration in this group rose in 10 days from 1.6 to 9.36 nmol.

Example 6

Piglets with Growth Deficit Using Free IAA in the Prestarter Feed

It is generally accepted that animals that have lower weights in early life have a lower performance all over the production period. The difference in early growth can, for a great deal, be explained by a difference in individual sensitivity to stress and/or infection pressure. This experiment was designed to study the effects of free IAA on the growth rate of healthy but poor growing pigs at an early stage of their life.

The test was carried out on a large commercial farm with 1400 sows in which poor-growing piglets were selected. The selected piglets were not suffering from any specific disease and piglets on the farm were tested negative for antibodies against PRRS (sows were vaccinated against PRRS). 39 Piglets were selected from a group of 600 at day 21 of age, seven days before weaning. These piglets were at random divided in three groups over three fostering sows until weaning. Two groups of piglets received free IAA in the prestarter feed in the farrowing period at a dose of 500 ug free IAA/kg LW/day. After weaning, free IAA was supplemented to these two groups in the starter feed at the same dose until 14 days after weaning. The amount of free IAA added to the feed was based on the estimated weights and feed intake. The third group received the same feed, but without free IAA.

The animals were weighed at weaning and 14 days later and mortality was monitored. The weight developments of the three groups are given in Table 12.

TABLE 12

| | Weight and growth of the piglets | | |
|---|---|---|---|
| | Number of animals in | Average weight (kg) | | Average weight |
| Day | each group | Day 28 (weaning) | Day 42 | gain (g/day) |
| Group 1, Control | 16 | 4.31 | 5.7 | 99 |
| Group 2, free IAA | 12 | 3.35 | 5.0 | 117 |
| Group 3, free IAA | 11 | 4.22 | 6.2 | 141 |

The groups treated with free IAA performed better than the control group; both groups 2 and 3 gained more weight than the control group. Free IAA clearly improved the performance of poor-growing piglets. In the control group, two animals died versus none in the free IAA treated groups.

Poorly growing piglets (runts) are often taken out of production because of poor performance and anticipated high medication costs. Treatment with free IAA may contribute to save these animals, to lower their medication costs and to improve performance and economics of a farm.

Example 7

Effect of Different Concentrations of Free IAA on African Catfish

A number of 360 African catfish (*Clarias gariepinus*) of approximately 30 grams each were used in this trial. One week after arrival, the fish were spread randomly over 12 identical aquaria, 30 fish in each aquarium. The temperature of the water was set at 25° C. and illumination schedule was 12 hours light followed by 12 hours darkness. The water circulation was 2 liters per aquarium per hour; the volume of water in each aquarium was adapted to the biomass. To get used to the feed, the fish were fed the basic feed during two weeks prior to the start of the trial.

Four groups were formed, each consisting of 90 fish divided over three aquaria. One group received no treatment and served as a control. The other three groups received free IAA treatment in three different doses as indicated in Table 13. Feed was prepared by mixing free IAA with basic feed in the concentrations indicated in Table 13. There was a fixed amount of feed given to the fish each day corresponding to 2.5% of the biomass.

TABLE 13

| Group | Feed given (mg free IAA/kg feed) | Dose based on actual feed intake of 2.5% of live weight (ug free IAA/kg LW/day) |
|---|---|---|
| 1 | 0 | 0 |
| 2 | 40 | 1360 |
| 3 | 16 | 544 |
| 4 | 6.4 | 218 |

The trial period lasted for five weeks and the fish were weighed every week. The average growth over the whole trial period is given in Table 14 below.

TABLE 14

| Group | Dose (ug free IAA/kg LW/day) | Average growth (g/d) |
|---|---|---|
| 1 | 0 | 4.96 |
| 2 | 1360 | 5.02 |
| 3 | 544 | 4.97 |
| 4 | 218 | 5.31 |

The results show that Group 4 (the dose of 218 ug free IAA/kg LW/day) gave a clear and significant improvement of 7.1% over the control at the same feed intake. Because all fish received exactly the same amount of feed, this means that also the feed conversion rate was improved with the same level. This is a significant increase for the fish industry and reflects the potential of free IAA in the stimulation of growth of healthy fish. The higher dosages did not show any clear positive or negative response in comparison to the control. It may, therefore, be concluded that an optimal dose for this kind of treatment is to be determined empirically.

Example 8

Preferred Stock Mixtures of IAA

A stock of a 4% free IAA feed stock additive was prepared. For that purpose, free IAA (Aldrich) was mixed with 94% protamyl and 2% yeast extract. From that stock, 1.25% was added to a feed additive as detailed below in Table 15.

TABLE 15

| Compound | % | kg |
|---|---|---|
| 4% IAA stock | 1.25 | 0.625 |
| Fe-sulphate | 0.5 | 0.25 |
| Protamyl | 5 | 2.5 |
| WPC 35 | 45 | 22.5 |
| Vitamin C | 2.5 | 1.25 |
| Maltodextrose | 45.55 | 22.775 |
| Vitamin E | 0.2 | 0.1 |
| SUM | 100 | 50 |

The feed additive according to Table 15 may be added to animal feed in appropriate amounts to ensure the desired dose to be administered to an animal. It may be apparent that the concentration in the feed may vary depending on the daily intake of feed of the animal as well as on the animal's weight. In order to supply an animal of 10 kg with a daily intake of 500 ug free IAA per kg LW, an amount of 10 grams of the mixture of Table 15 may be mixed with the amount of feed that the animal ingests per day.

What is claimed is:

1. A method of treating low IGF-1 serum level in a non-human animal, the method comprising:
   identifying a non-human animal having low IGF-1 serum level; and
   treating the non-human animal having low IGF-1 serum level with free indole acetic acid (IAA) or a derivative thereof wherein the derivative is selected from the group consisting of 4-hydroxy-IAA, 4-methoxy-IAA, 5-hydroxy-IAA, 5-methoxy-IAA, 6-hydroxy-IAA, 6-methoxy-IAA, 7-hydroxy-IAA, and 7-methoxy-IAA, thereby increasing the serum levels of IGF-1 in the non-human animal.

2. The method according to claim 1, wherein treating the non-human animal comprises administering to the non-human animal a therapeutic composition comprising free IAA or the derivative thereof.

3. The method according to claim 1, wherein the non-human animals have at least one of a growth deficit and or a weakened immune system.

4. The method according to claim 1 wherein the non-human animals have at least one of a growth deficit or a weakened immune system.

5. The method according to claim 1, wherein the non-human animal having low IGF-1 serum level has an IGF-1 serum level that is at least 10%, below the normal median IGF-1 serum level of a healthy non-human animal of the same species.

6. The method according to claim 1, wherein treating the non-human animal having low IGF-1 serum level with free IAA or a derivative thereof comprises administering to the non-human animal a feed composition comprising free IAA or a derivative thereof.

7. The method according to claim 1, the method further comprising measuring the IGF-1 serum level of the non-human animal after treating the non-human animal having low IGF-1 serum level with free IAA or a derivative thereof.

8. The method according to claim 7, wherein the IGF-1 serum level is measured 10 days after treating the non-human animal having low IGF-1 serum level with free IAA or a derivative thereof.

9. The method according to claim 1, wherein treating the non-human animal having low IGF-1 serum level with free IAA or a derivative thereof comprises treating the animal with free IAA or a derivative thereof for at least 2 weeks.

10. The method according to claim 1, wherein the non-human animal having low IGF-1 serum level has an IGF-1 serum level that is at least 25% below the normal median IGF-1 serum level of a healthy non-human animal of the same species.

11. The method according to claim 1, wherein the non-human animal having low IGF-1 serum level has an IGF-1 serum level that is at least 40% below the normal median IGF-1 serum level of a healthy non-human animal of the same species.

12. The method according to claim 1, wherein the non-human animal having low IGF-1 serum level has an IGF-1 serum level that is at least 60% below the normal median IGF-1 serum level of a healthy non-human animal of the same species.

13. The method according to claim 1, wherein the non-human animal having low IGF-1 serum level has an IGF-1 serum level that is at least 80% below the normal median IGF-1 serum level of a healthy non-human animal of the same species.

14. The method according to claim 8, wherein the IGF-1 serum level is measured 26 days after treating the non-human animal having low IGF-1 serum level with free IAA or a derivative thereof.

15. The method according to claim 8, wherein the IGF-1 serum level is measured 31 days after treating the non-human animal having low IGF-1 serum level with free IAA or a derivative thereof.

16. The method according to claim 1, wherein treating the non-human animal having low IGF-1 serum level with free IAA or a derivative thereof comprises treating the animal with free IAA or a derivative thereof for at least 3 weeks.

17. The method according to claim 1, wherein treating the non-human animal having low IGF-1 serum level with free IAA or a derivative thereof comprises treating the animal with free IAA or a derivative thereof for at least 4 weeks.

18. The method according to claim 1, wherein treating the non-human animal having low IGF-1 serum level with free IAA or a derivative thereof comprises treating the animal with free IAA or a derivative thereof for at least 6 weeks.

19. The method according to claim 6, wherein the feed composition comprises from 240 micrograms/kilogram to 40 grams/kilogram of the free IAA or derivative thereof.

20. The method according to claim 6, wherein the feed composition comprises from 100 mg/kg to 1000 mg/kilogram of the free IAA or derivative thereof.

21. The method according to claim 1, wherein the treating the non-human animal having low IFG-2 serum level with free IAA or a derivative thereof comprises administering to the non-human animal a amount selected from the group consisting of 25 to 1000, 50 to 500, 150 to 500, 50 to 1000, 250 to 1000, 400 to 1000, and 750 to 1000 micrograms/kg life weight/day of the free IAA or derivative thereof.

* * * * *

UNITED STATES PATENT AND TRADEMARK OFFICE
CERTIFICATE OF CORRECTION

PATENT NO. : 8,883,233 B2
APPLICATION NO. : 13/549119
DATED : November 11, 2014
INVENTOR(S) : Hubert Jean-Marie François Gillessen et al.

It is certified that error appears in the above-identified patent and that said Letters Patent is hereby corrected as shown below:

On the title page:
In ITEM (75) Inventors: change "Hurbert Jean Marie Francois Gillessen," to --Hubert Jean Marie François Gillessen,--

In ITEM (56) References Cited:
 OTHER PUBLICATIONS
  Page 1, 2nd column, 3rd line of the 3rd entry (line 40), at the end of the line change "A phase II study (11-19-20012).*" to --A phase II study (11-19-2002).*--

In the specification:

| | | |
|---|---|---|
| COLUMN 3, | LINE 66, | change "5 mg/I" to --5 mg/l-- |
| COLUMN 3, | LINE 67, | change "2.5 mg/I" to --2.5 mg/l-- |
| COLUMN 4, | LINE 54, | change "120 ug free" to --120 µg free-- |
| COLUMN 4, | LINE 56, | change "1000 ug/I." to --1000 µg/l.-- |
| COLUMN 5, | LINE 28, | change "IGF-1 Provided" to --IGF-1. Provided-- |
| COLUMN 5, | LINE 46, | change "ug/kg LW/day" to --µg/kg LW/day-- |
| COLUMN 5, | LINE 48, | change "500 ug free" to --500 µg free-- |
| COLUMN 5, | LINE 50, | change "218 ug free" to --218 µg free-- |
| COLUMN 5, | LINE 52, | change "400 ug free" to --400 µg free-- |
| COLUMN 5, | LINE 58, | change "1000 ug free" to --1000 µg free-- |
| COLUMN 5, | LINE 59, | change "1000 ug free" to --1000 µg free-- |
| COLUMN 5, | LINE 60, | change "1000 ug free" to --1000 µg free-- |
| COLUMN 5, | LINE 61, | change "1000 ug free" to --1000 µg free-- |
| COLUMN 6, | LINE 52, | change "1.2 ug/g" to --1.2 µg/g-- |
| COLUMN 6, | LINE 53, | change "Arabidopsis." to --*Arabidopsis.*-- |
| COLUMN 9, | LINE 40, | change "1 g/I," to --1 g/l,-- |
| COLUMN 9, | LINE 41, | change "nonojet" to --NANOJET®-- |
| COLUMN 10, | LINE 2, | change "500 ug free" to --500 µg free-- |

Signed and Sealed this
Twenty-third Day of June, 2015

Michelle K. Lee
*Director of the United States Patent and Trademark Office*

CERTIFICATE OF CORRECTION (continued)
U.S. Pat. No. 8,883,233 B2

In the specification (continued):

| | | |
|---|---|---|
| COLUMN 11, | LINE 22, | change "500 ug free" to --500 μg free-- |
| COLUMN 11, | LINE 45, | change "400 ug free" to --400 μg free-- |
| COLUMN 12, | LINE 42, | change "400 ug free" to --400 μg free-- |
| COLUMN 13, | LINE 24, | change "400 ug free" to --400 μg free-- |
| COLUMN 13, | LINE 67, | change "715 ug free" to --715 μg free-- |
| COLUMN 16, | LINE 14, | change "500 ug free" to --500 μg free-- |
| COLUMN 17, | LINE 29, | change "218 ug free" to --218 μg free-- |
| COLUMN 18, | LINE 2, | change "ug free IAA" to --μg free IAA-- |

In the claims:

CLAIM 3, COLUMN 18, LINE 24, at the end of the line change "at least one of a growth deficit and or a" to --at least one of a growth deficit or a--

CLAIM 4, COLUMN 18, LINE 27, at the end of the line change "at least one of a growth deficit and or a" to --at least one of a growth deficit or a--